US010533203B2

(12) United States Patent
Carlson

(10) Patent No.: US 10,533,203 B2
(45) Date of Patent: Jan. 14, 2020

(54) SYSTEM FOR THE TREATMENT OF BIOMASS

(75) Inventor: David Charles Carlson, Yankton, SD (US)

(73) Assignee: POET Research, Inc., Sioux Falls, SD (US)

( * ) Notice: Subject to any disclaimer, the term of this patent is extended or adjusted under 35 U.S.C. 154(b) by 0 days.

(21) Appl. No.: 13/638,238

(22) PCT Filed: Mar. 18, 2011

(86) PCT No.: PCT/US2011/029047
§ 371 (c)(1),
(2), (4) Date: Sep. 28, 2012

(87) PCT Pub. No.: WO2011/116317
PCT Pub. Date: Sep. 22, 2011

(65) Prior Publication Data
US 2013/0065289 A1  Mar. 14, 2013

Related U.S. Application Data

(60) Provisional application No. 61/315,830, filed on Mar. 19, 2010.

(51) Int. Cl.
C12P 19/14 (2006.01)

(52) U.S. Cl.
CPC .................... C12P 19/14 (2013.01)

(58) Field of Classification Search
CPC ........ B01D 2311/04; B01D 2311/2688; B01D 2317/025; B01D 61/58; C12M 45/04; C12M 21/04; C12M 43/08; C12M 21/12; C12M 23/58; C12M 43/02; C12M 45/09; C12P 2201/00; C12P 7/10; Y02E 50/17; Y02E 50/343; Y02E 50/16; A23K 10/12; A23L 7/104; C13K 1/02
USPC ........................................ 435/161
See application file for complete search history.

(56) References Cited

U.S. PATENT DOCUMENTS

| 3,212,932 A | 10/1965 | Hess et al. |
| 4,014,743 A | 3/1977 | Black |
| 4,029,515 A | 6/1977 | Kiminki et al. |
| 4,152,197 A | 5/1979 | Lindahl et al. |
| 4,168,988 A | 9/1979 | Riehm et al. |
| 4,342,831 A | 8/1982 | Faber et al. |
| 4,425,433 A | 1/1984 | Neves |
| 4,427,453 A | 1/1984 | Reitter |
| 4,432,805 A | 2/1984 | Nuuttila et al. |
| 4,461,648 A | 7/1984 | Foody |
| 4,529,699 A | 7/1985 | Gerez et al. |
| 4,552,616 A | 11/1985 | Kauppi |
| 4,612,286 A | 9/1986 | Sherman et al. |
| 4,668,340 A | 5/1987 | Sherman |
| 4,752,579 A | 6/1988 | Arena et al. |
| 4,908,098 A | 3/1990 | DeLong et al. |
| 4,941,944 A | 7/1990 | Chang |
| 4,997,488 A | 3/1991 | Gould et al. |
| 5,125,977 A | 6/1992 | Grohmann et al. |
| 5,171,592 A | 12/1992 | Holtzapple et al. |
| 5,221,357 A | 6/1993 | Brink |
| 5,328,562 A | 7/1994 | Rafferty et al. |
| 5,338,366 A | 8/1994 | Grace et al. |
| 5,366,558 A | 11/1994 | Brink |
| 5,370,999 A | 12/1994 | Stuart |
| 5,411,594 A | 5/1995 | Brelsford |
| 5,424,417 A | 6/1995 | Torget et al. |
| 5,498,766 A | 3/1996 | Stuart et al. |
| 5,536,325 A | 7/1996 | Brink |
| 5,562,777 A | 10/1996 | Farone et al. |
| 5,580,389 A | 12/1996 | Farone et al. |
| 5,597,714 A | 1/1997 | Farone et al. |
| 5,628,830 A | 5/1997 | Brink |
| 5,693,296 A | 12/1997 | Holtzapple et al. |
| 5,705,369 A | 1/1998 | Torget et al. |
| 5,711,817 A | 1/1998 | Titmas |
| 5,726,046 A | 3/1998 | Farone et al. |
| 5,733,758 A | 3/1998 | Nguyen |
| 5,769,934 A | 6/1998 | Ha et al. |
| 5,782,982 A | 7/1998 | Farone et al. |
| 5,820,687 A | 10/1998 | Farone et al. |
| 5,865,898 A | 2/1999 | Holtzapple et al. |

(Continued)

FOREIGN PATENT DOCUMENTS

| EP | 0 044 658 | 1/1982 |
| EP | 0 098 490 | 1/1984 |

(Continued)

OTHER PUBLICATIONS

Marchal et al. Large-scale enzymatic hydrolysis of agricultural lignocellulosic biomass. Part 2: conversion into acetone-butanol. Bioresource Technology. 1992;42:205-217.*
Larsen et al. The IBUS process—lignocellulosic bioethanol close to a commercial reality. Chem. Eng. Technol. 2008;31(5):765-772.*
Sun et al. Hydrolysis of lignocellulosic materials for ethanol production: a review. Bioresource Technology. 2002;83:1-11.*
Haagensen et al. Enzymatic hydrolysis and glucose fermentation of wet oxidized sugarcane bagasse and rice straw for bioethanol production. Riso-R-1517 (EN). 2002;1:184-195.*

(Continued)

Primary Examiner — Lynn Y Fan

(74) Attorney, Agent, or Firm — Kagan Binder, PLLC

(57) ABSTRACT

A system for treating biomass for the production of ethanol is disclosed. A biorefinery for producing a fermentation product from biomass is disclosed. The biorefinery comprises a system for preparing the biomass into prepared biomass and a system for pre-treating the biomass into pre-treated biomass. The biorefinery comprises a separator, a first treatment system, a second treatment system, and a fermentation system. A method for producing a fermentation product from biomass is disclosed.

12 Claims, 13 Drawing Sheets

(56) References Cited

U.S. PATENT DOCUMENTS

| | | |
|---|---|---|
| 5,879,463 A | 3/1999 | Proenca |
| 5,916,780 A | 6/1999 | Foody et al. |
| 5,932,452 A | 8/1999 | Mustranta et al. |
| 5,932,456 A | 8/1999 | Van Draanen et al. |
| 5,972,118 A | 10/1999 | Hester et al. |
| 5,975,439 A | 11/1999 | Chieffalo et al. |
| 6,022,419 A | 2/2000 | Torget et al. |
| 6,090,595 A | 7/2000 | Foody et al. |
| 6,228,177 B1 | 5/2001 | Torget |
| 6,379,504 B1 | 4/2002 | Miele et al. |
| 6,419,788 B1 | 7/2002 | Wingerson |
| 6,423,145 B1 | 7/2002 | Nguyen et al. |
| 6,555,350 B2 | 4/2003 | Ahring et al. |
| 6,620,292 B2 | 9/2003 | Wingerson |
| 6,660,506 B2 | 12/2003 | Nguyen et al. |
| 6,692,578 B2 | 2/2004 | Schmidt et al. |
| 6,770,168 B1 | 8/2004 | Stigsson |
| 7,198,925 B2 | 4/2007 | Foody |
| 7,238,242 B2 | 7/2007 | Pinatti et al. |
| 7,354,743 B2 | 4/2008 | Vlasenko et al. |
| 7,455,997 B2 | 11/2008 | Hughes |
| 7,501,025 B2 | 3/2009 | Bakker et al. |
| 7,503,981 B2 | 3/2009 | Wyman et al. |
| 7,585,652 B2 | 9/2009 | Foody et al. |
| 7,604,967 B2 | 10/2009 | Yang et al. |
| 7,649,086 B2 | 1/2010 | Belanger et al. |
| 7,666,637 B2 | 2/2010 | Nguyen |
| 7,670,813 B2 | 3/2010 | Foody et al. |
| 7,709,042 B2 | 5/2010 | Foody et al. |
| 7,754,456 B2 | 7/2010 | Penttila et al. |
| 7,754,457 B2 | 7/2010 | Foody et al. |
| 7,807,419 B2 | 10/2010 | Hennessey et al. |
| 7,815,741 B2 | 10/2010 | Olson |
| 7,815,876 B2 | 10/2010 | Olson |
| 7,819,976 B2 | 10/2010 | Friend et al. |
| 7,875,444 B2 | 1/2011 | Yang et al. |
| 7,901,511 B2 | 3/2011 | Griffin et al. |
| 8,057,639 B2 | 11/2011 | Pschorn et al. |
| 8,057,641 B2 | 11/2011 | Bartek et al. |
| 8,110,383 B2 | 2/2012 | Jönsson et al. |
| 8,123,864 B2 | 2/2012 | Christensen et al. |
| 8,288,600 B2 | 10/2012 | Bartek et al. |
| 8,449,728 B2 | 5/2013 | Redford |
| 8,597,431 B2 | 12/2013 | McDonald et al. |
| 8,815,552 B2 | 8/2014 | Narendranath et al. |
| 9,139,857 B2 | 9/2015 | Retsina et al. |
| 10,174,351 B2 | 1/2019 | Smits et al. |
| 2002/0192774 A1 | 12/2002 | Ahring et al. |
| 2004/0060673 A1 | 4/2004 | Phillips et al. |
| 2004/0252580 A1* | 12/2004 | Nagy et al. ............ 366/241 |
| 2005/0069998 A1 | 3/2005 | Ballesteros Perdices et al. |
| 2006/0188965 A1* | 8/2006 | Wyman et al. ............ 435/72 |
| 2006/0281157 A1 | 12/2006 | Chotani et al. |
| 2008/0026431 A1 | 1/2008 | Saito et al. |
| 2008/0057555 A1 | 3/2008 | Nguyen |
| 2008/0277082 A1 | 11/2008 | Pschorn et al. |
| 2008/0295981 A1 | 12/2008 | Shin et al. |
| 2009/0035826 A1 | 2/2009 | Tolan et al. |
| 2009/0042259 A1 | 2/2009 | Dale et al. |
| 2009/0098616 A1 | 4/2009 | Burke et al. |
| 2009/0308383 A1 | 12/2009 | Shin et al. |
| 2010/0003733 A1 | 1/2010 | Foody et al. |
| 2010/0144001 A1 | 6/2010 | Horton |
| 2010/0233771 A1 | 9/2010 | McDonald et al. |
| 2010/0285553 A1 | 11/2010 | Delmas et al. |
| 2011/0011391 A1 | 1/2011 | Burke |
| 2011/0079219 A1 | 4/2011 | McDonald et al. |
| 2011/0094505 A1 | 4/2011 | Bulla et al. |
| 2011/0171708 A1 | 7/2011 | Larsen |
| 2012/0027027 A1 | 2/2012 | Yamaura et al. |
| 2012/0129234 A1 | 5/2012 | McDonald et al. |
| 2012/0138246 A1 | 6/2012 | Christensen et al. |
| 2012/0201947 A1 | 8/2012 | Stuart |
| 2013/0143290 A1 | 6/2013 | Narendranath |
| 2013/0164804 A1 | 6/2013 | Walther et al. |
| 2013/0337521 A1 | 12/2013 | Carlson et al. |
| 2014/0024826 A1 | 1/2014 | Narendranath et al. |
| 2014/0209092 A1 | 7/2014 | McDonald et al. |
| 2014/0234911 A1 | 8/2014 | Narendranath et al. |
| 2015/0128932 A1 | 5/2015 | Kwiatkowski et al. |

FOREIGN PATENT DOCUMENTS

| | | | |
|---|---|---|---|
| EP | 0 159 795 | 10/1985 | |
| EP | 0 884 391 | 12/1998 | |
| EP | 1 259 466 | 11/2002 | |
| EP | 1 130 085 | 10/2005 | |
| FR | 2 397 486 | 2/1979 | |
| FR | 2 609 046 | 7/1988 | |
| WO | WO 94/08027 | 4/1994 | |
| WO | WO 94/29475 | 12/1994 | |
| WO | WO 95/08648 | 3/1995 | |
| WO | WO 98/14270 | 4/1998 | |
| WO | WO 98/56958 | 12/1998 | |
| WO | WO 99/06133 | 2/1999 | |
| WO | WO 00/14120 | 3/2000 | |
| WO | WO 00/61858 | 10/2000 | |
| WO | WO 00/073221 | 12/2000 | |
| WO | WO 01/32715 | 5/2001 | |
| WO | WO 01/60752 | 8/2001 | |
| WO | WO 02/14598 | 2/2002 | |
| WO | WO 02/24882 | 3/2002 | |
| WO | WO 02/38786 | 5/2002 | |
| WO | WO 02/051561 | 7/2002 | |
| WO | WO 02/067691 | 9/2002 | |
| WO | WO 02/070753 | 9/2002 | |
| WO | WO 03/013714 | 2/2003 | |
| WO | WO 03/071025 | 8/2003 | |
| WO | WO 03/078644 | 9/2003 | |
| WO | WO 2004/081193 | 9/2004 | |
| WO | WO 2005/099854 | 10/2005 | |
| WO | 2005118828 A1 | 12/2005 | |
| WO | WO2005118828 * | 12/2005 | ............ C12P 7/10 |
| WO | WO 2006/032282 | 3/2006 | |
| WO | WO 2006/034590 | 4/2006 | |
| WO | WO 2006/056838 | 6/2006 | |
| WO | WO2006101832 * | 9/2006 | ............ C12P 7/06 |
| WO | WO 2007/009463 | 1/2007 | |
| WO | WO 2008/095098 | 8/2008 | |
| WO | WO 2008/131229 | 10/2008 | |
| WO | WO 2009/003167 | 12/2008 | |
| WO | WO 2009/045651 | 4/2009 | |
| WO | 2009090480 A2 | 7/2009 | |
| WO | 2009/095781 A1 | 8/2009 | |
| WO | WO 2009/108773 | 9/2009 | |
| WO | WO 2010/071805 | 6/2010 | |
| WO | WO 2010/113129 | 10/2010 | |
| WO | WO 2010/113130 | 10/2010 | |
| WO | WO 2011/061400 | 5/2011 | |
| WO | WO 2011/116317 | 9/2011 | |
| WO | WO 2011/159915 | 12/2011 | |
| WO | 2012/027843 A1 | 3/2012 | |
| WO | WO 2012/042497 | 4/2012 | |
| WO | WO 2012/042498 | 4/2012 | |
| WO | WO 2012/103281 | 8/2012 | |
| WO | WO 2012/131665 | 10/2012 | |

OTHER PUBLICATIONS

Blunk et al. Combustion properties of lignin residue from lignocellulose fermentation. National Renewable Energy Laboratory. 2000;1-15.*

Aden et al. Lignocellulosic Biomass to Ethanol Process Design and Economics Utilizing Co-Current Dilute Acid Prehydrolysis and . NREL. 2002;1-154.*

Enzyme. Enzyme: 3.2.1.91. KEGG. 2005;1-6.*

International Search Report and Written Opinion for International Application No. PCT/US2011/029047 dated Jul. 18, 2011, 12 pages.

Marchal, et al., "Large-scale enzymatic hydrolysis of agricultural lignocellulosic biomass: Part 2. Conversion into acetone-butanol". Bioresource Technology, Elsevier BV, GB, vol. 42, No. 3, Jan. 1, 1992, pp. 205-217, XP002596773, ISSN: 0960-8524, p. 206, col. 1, figure 1, 14 pages.

(56) References Cited

OTHER PUBLICATIONS

Larsen, et al., "The IBUS Process—Lignocellulosic Bioethanol Close to a Commercial Reality". Chemical Engineering and Technology, Weinheim, DE, vol. 21, No. 5, Apr. 22, 2008, pp. 765-772, XP002517673, ISSN: 0930-7516, DOI:10.1002/CEAT.200800048, 8 pages.

Sun, et al., "Hydrolysis of lingnocellulosic materials for ethanol production: a review", Bioresource Technology, Elsevier BV, GB, vol. 83, Jan. 1, 2002, pp. 1-11, XP002988039, ISSN: 0960-8524, DOI: DOI10.1016/S0960-8524(01)00212-7, 11 pages.

Reith, J.H. et al. "Co-Production of Bio-Ethanol, Electricity and Heat From Biomass Residues", Contribution to the 12$^{th}$ European Conference and Technology Exhibition on Biomass for Energy, Industry and Climate Protection, Jun. 17-21, 2002, Amsterdam, the Netherlands, pp. 1-22.

Taherzadeh, M.J. et al. "Enzyme-Based Hydrolysis Processes for Ethanol From Lignocellulosic Materials: A Review", BioResources 2(4), 2007, pp. 707-738.

Thomsen, M.H. et al., "Preliminary Results on Optimization of Pilot Scale Pretreatment of Wheat Straw Used on Coproduction of Bioethanol and Electricity", Applied Biochemistry and Biotechnology, vol. 129-132, 2006, p. 448.

Varga, E., et al., "High Solid Simultaneous Saccharification and Fermentation of Wet Oxidized Corn Stover to Ethanol", Biotechnol. Bioeng. 88(5), 2004, Abstract.

Adney, B. et al., "Measurement of Cellulase Activities", Technical Report NREL/TP-510-42628 (2008) Cover; p. 1-8.

Caparros, S. et al., "Xylooligosaccharides Production from Arundo donax", J. Agric. Food Chem. 55 (2007): p. 5536-5543.

Cort, J. et al., "Minimize Scale-Up Risk", www.aiche.org/cep, (2010): p. 39-49.

Demain, A.L. et al., "Cellulase, Clostridia, and Ethanol", Microbiology and Molecular Biology Reviews 69(1) (2005): p. 124-154.

Dien, B.S. et al., "Enzyme characterization for hydrolysis of AFEX and liquid hot-water pretreated distillers' grains and their conversion to ethanol", Bioresource Technology 99 (2008): p. 5216-5225.

Gibbons, W.R. et al., "Fuel Ethanol and High Protein Feed from Corn and Corn-Whey Mixtures in a Farm-Scale Plant", Biotechnology and Bioengineering XXV (1983): p. 2127-2148.

Goodman, B. J., "FY 1988 Ethanol from Biomass Annual Report" (1989): p. 1-458.

Grohmann, K. et al., "Optimization of Dilute Acid Pretreatment of Biomass", Biotechnology and Bioengineering Symp. 15 (1985): p. 59-80.

Grohmann, K. et al., "Dilute Acid Pretreatment of Biomass at High Solids Concentrations", Biotechnology and Bioengineering Symp. 17 (1986): p. 135-151.

Humbird, D. et al., "Process Design and Economics for Biochemical Conversion of Lignocellulosic Biomass to Ethanol: Dilute-Acid Pretreatment and Enzymatic Hydrolysis of Corn Stover", National Renewable Energy Laboratory (2011): Covers with Introduction; p. 1-114.

Jeoh, T. "Steam Explosion Pretreatment of Cotton Gin Waste for Fuel Ethanol Production", Thesis submitted to Virginia Polytechnic Institute and State University (1998): Cover with Introduction; p. 1-138.

Jorgensen, H. et al., "Enzymatic conversion of lignocellulose into fermentable sugars: challenges and opportunities", Biofuels, Bioprod. Bioref. 1 (2001): p. 119-134.

Kumar, R. et al., "Effect of Enzyme Supplementation at Moderate Cellulase Loadings on Initial Glucose and Xylose Release from Corn Stover Solids Pretreated by Leading Technologies", Biotechnology and Bioengineering 102(2) (2009): p. 457-467.

Lynd, L.R. et al. "Consolidated bioprocessing of cellulosic biomass: an update", Current Opinion in Biotechnology 16 (2005): p. 577-583.

Mosier, N. et al., "Features of promising technologies for pretreatment of lignocellulosic biomass", Bioresource Technology 96 (2005): p. 673-686.

McMillan, J.D. "Processes for Pretreating Lignocellulosic Biomass: A Review", National Renewable Energy Laboratory (1992): Covers with Introduction; p. 1-44.

Nandini, C. et al. "Carbohydrate composition of wheat, wheat bran, sorghum and bajra with good chapatti/roti (Indian flat bread) making quality", Food Chemistry 73 (2001): p. 197-203.

Sanchez, O.J. et al., "Trends in biotechnological production of fuel ethanol from different feedstocks", Bioresource Technology 99 (2008): p. 5270-5295.

Saska, M. et al., "Aqueous Extraction of Sugarcane Bagasse Hemicellulose and Production of Xylose Syrup", Biotechnology and Bioengineering 45 (1995): p. 517-523.

Sepulveda-Huerta, E. et al. "Production of detoxified sorghum straw hydrolysates for fermentative purposes", Journal of the Science of Food and Agriculture 86 (2006): p. 2579-2586.

Spindler, D. et al., "Evaluation of Pretreated Woody Crops for the Simultaneous Saccharification and Fermentation Process", Ethanol from Biomass. FY 1988, Annual Report (1989): p. B33-B43.

Taherzadeh, M.J. et al., "Acid-based Hydrolysis Processes for Ethanol from Lignocellulosic Materials: A Review", BioResources 2(3) (2007): p. 472-499.

Taherzadeh, M.J. et al., "Enzyme-based Hydrolysis Processes for Ethanol from Lignocellulosic Materials: A Review", BioResources 2(4) (2007): p. 707-738.

Texeira, R.H. et al., "Ethanol Annual Report FY 1990", (1991): p. 1-346.

Torget, R. et al., "Dilute Acid Pretreatment of Short Rotation Woody and Herbaceous Crops", Applied Biochemistry and Biotechnology 24/25 (1990): p. 115-126.

Torget, R. et al., "Initial Design of a Dilute Sulfuric Acid Pretreatment Process for Aspen Wood Chips", Solar Energy Research Institute (1988): p. 89-104.

Torget, R. et al., "Dilute Acid Pretreatment of Corn Cobs, Corn Stover, and Short-Rotation Crops", FY 1990 Ethanol Annual Report (1991): p. 71-82.

Weil, J. et al., "Pretreatment of Corn Fiber by Pressure Cooking in Water", Applied Biochemistry and Biotechnology 73 (1998): p. 1-17.

Wyman, Charles E., "What is (and is not) vital to advancing cellulosic ethanol", Trends in Biotechnology 25(4) (2007): p. 153-157.

Wyman, C.E. et al., "Coordinated development of leading biomass pretreatment technologies", Bioresource Technology 96 (2005): p. 1959-1966.

Yang, B. et al., "Pretreatment: the key to unlocking low-cost cellulosic ethanol", Biofuels, Bioprod. Bioref. 2 (2008): p. 26-40.

Zhang, Y-H.P. et al., "Outlook for cellulose improvement: Screening and selection strategies", Biotechnology Advances 24 (2006): p. 452-481.

Zhang, Y.P. et al., "Toward an Aggregated Understanding of Enzymatic Hydrolysis of Cellulose: Noncomplexed Cellulase Systems", Biotechnology and Bioengineering 88(7) (2004): p. 797-824.

U.S. Appl. No. 12/716,989, filed Mar. 2010, Kwiatkowski.
U.S. Appl. No. 12/827,948, filed Jun. 2010, Bootsma et al.
U.S. Appl. No. 13/209,170, filed Aug. 2011, Bly et al.
U.S. Appl. No. 14/459,977, filed Aug. 2014, Bootsma.
U.S. Appl. No. 14/465,177, filed Aug. 2014, Narendranath et al.

Bura, R. et al., "Influence of Xylan on the Enzymatic Hydrolysis of Steam-Pretreated Corn Stover and Hybrid Poplar", Biotechnol. Prog. 25(2) (2009): p. 315-322.

Cara, C. et al., "Influence of solid loading on enzymatic hydrolysis of steam exploded or liquid hot water pretreated olive tree biomass", Process Biochemistry 42 (2007): p. 1003-1009.

Gao, D. et al., "Strategy for Identification of Novel Fungal and Bacterial Glycosyl Hydrolase Hybrid Mixtures that can Efficiently Saccharify Pretreated Lignocellulosic Biomass", Bioenerg. Res. 3 (2010): p. 67-81.

Guo, G.L. et al., "Characterization of enzymatic saccharification for acid-pretreated lignocellulosic materials with different lignin composition", Enzyme and Microbial Technology 45 (2009): p. 80-87.

Kumar, S. et al., "Recent Advances in Production of Bioethanol from Lignocellulosic Biomass", Chem. Eng. Technol. 32(4) (2009): p. 517-526.

(56) References Cited

OTHER PUBLICATIONS

Li, X.L. et al., "Two cellulases, CelA and Ce1C, from the polycentric anaerobic fungus Orpinomyces strain PC-2 contain N-terminal docking domains for a cellulose-hemicellulase complex", Applied and Environmental Microbiology 63(12) (1997): p. 4721-4728.

Olsson, L. et al., "Fermentation of lignocellulosic hydrolysates or ethanol production", Enzyme Microb. Technol., 18 (1996): p. 312-331.

Xiao, Z. et al., "Effects of Sugar Inhibition on Cellulases and β-Glucosidase During Enzymatic Hydrolysis of Softwood Substrates", Applied Biochemistry and Biotechnology 113-116 (2004): p. 1115-1126.

Communication pursuant to Article 94(3) EPC for European Application No. 11710394.5, dated Mar. 8, 2017 (5 pages).

\* cited by examiner

FIG. 8A
Biomass Composition

| Cob (percent) | Husks/ Leaves (percent) | Stalk (percent) | Cellulose (Glucan) (percent) | Hemicellulose Xylan (percent) | Arabinan (percent) | Acetate (percent) | Composite (percent) | Lignin (percent) | Ash (percent) |
|---|---|---|---|---|---|---|---|---|---|
| 100 | 0 | 0 | 35.0 | 33.3 | 3.6 | 3.0 | 39.9 | 14.9 | 2.2 |
| 0 | 100 | 0 | 37.2 | 25.6 | 4.9 | 2.2 | 32.7 | 13.0 | 7.7 |
| 0 | 0 | 100 | 41.7 | 22.5 | 2.4 | 2.6 | 27.5 | 16.3 | 3.7 |
| 50 | 0 | 50 | 38.8 | 27.9 | 3.0 | 2.8 | 33.7 | 16.6 | 3.0 |
| 50 | 50 | 0 | 36.6 | 29.5 | 4.2 | 2.6 | 36.3 | 14.0 | 5.0 |
| 30 | 50 | 20 | 37.7 | 27.3 | 4.0 | 2.5 | 33.8 | 14.6 | 5.3 |

FIG. 8B
Biomass

| | Cellulose (Glucan) (percent) (approx.) | Hemicellulose (percent) (approx.) | Lignin (percent) (approx.) | Ash (percent) (approx.) |
|---|---|---|---|---|
| Typical Range | 35-45 | 24-42 | 12-20 | 2-6 |
| Expected Range | 30-55 | 20-50 | 10-25 | 1-10 |

FIG. 9A
Pre-Treated Biomass Liquid Component Composition

| Cob (percent) | Husks/ Leaves (percent) | Stalk (percent) | Glucose (percent) | Xylose (percent) | Arabinose (percent) | Acetic Acid (ppm) |
|---|---|---|---|---|---|---|
| 100 | 0 | 0 | 0.4 | 4.8 | 0.5 | 6090 |
| 0 | 100 | 0 | 0.4 | 2.7 | 0.5 | 3400 |
| 0 | 0 | 100 | 0.4 | 4.2 | 0.4 | 6180 |
| 50 | 0 | 50 | 0.4 | 4.5 | 0.4 | 6125 |
| 30 | 50 | 20 | 0.4 | 3.6 | 0.5 | 4763 |

FIG. 9B
Pre-Treated Biomass
Liquid Component

|  | Glucose (percent) (approx.) | Xylose (percent) (approx.) | Arabinose (percent) (approx.) | Acetic Acid (ppm) (approx.) |
|---|---|---|---|---|
| Typical Range | 0-1 | 2-6 | 0-1 | 3000-6400 |
| Expected Range | 0-1 | 1-8 | 0-1 | 2000-8000 |

FIG. 10A
Pre-Treated Biomass
Solids Component Composition

| Cob (percent) | Husks/ Leaves (percent) | Stalk (percent) | Cellulose (Glucan) (percent) | Hemicellulose | | | | Lignin (percent) | Ash (percent) |
|---|---|---|---|---|---|---|---|---|---|
|  |  |  |  | Xylan (percent) | Arabinan (percent) | Acetate (percent) | Composite (percent) |  |  |
| 100 | 0 | 0 | 60.2 | 9.5 | 0.9 | 0.3 | 10.7 | 26.7 | 1.2 |
| 0 | 100 | 0 | 54.4 | 1.3 | 0.7 | 0.7 | 10.4 | 23.8 | 9.7 |
| 0 | 0 | 100 | 51.1 | 1.4 | 1.0 | 1.0 | 15.4 | 27.3 | 3.1 |
| 50 | 0 | 50 | 56.7 | 5.5 | 0.9 | 0.6 | 13.1 | 27.0 | 2.2 |
| 50 | 50 | 0 | 57.3 | 5.4 | 0.8 | 0.5 | 10.5 | 25.2 | 5.4 |
| 30 | 50 | 20 | 55.5 | 3.8 | 0.8 | 0.6 | 11.5 | 25.4 | 5.8 |

FIG. 10B
Pre-Treated Biomass
Solids Component

|  | Cellulose (Glucan) (percent) (approx.) | Hemicellulose (percent) (approx.) | Lignin (percent) (approx.) | Ash (percent) (approx.) |
|---|---|---|---|---|
| Typical Range | 48-62 | 8-17 | 22-30 | 1-10 |
| Expected Range | 45-65 | 5-20 | 20-32 | 1-10 |

FIG. 11

| Pretreatment | |
|---|---|
| Sulfuric Acid Concentration | 1.3 percent by weight |
| Temperature | 120 degrees Celsius |
| Time | 120 minutes |
| Acid solution (L/S ratio) | 7 g acid solution /g biomass |

| Enzymatic Liquefaction | |
|---|---|
| Enzyme Loading | 6.0 mg protein/g glucan |
| Temperature | 50 degrees Celsius |
| pH | 5.7 |
| Solids Loading | 15.0 percent by weight |
| Time | 10 hours |

US 10,533,203 B2

SYSTEM FOR THE TREATMENT OF BIOMASS

CROSS-REFERENCE TO RELATED APPLICATIONS

This application is a U.S. national stage filing of Patent Cooperation Treaty (PCT) application serial number PCT/US11/29047 entitled "SYSTEM FOR TREATMENT OF BIOMASS" filed on Mar. 18, 2011, which claims the benefit of U.S. Provisional Application Ser. No. 61/315,830, entitled "SYSTEM FOR TREATMENT OF BIOMASS", filed on Mar. 19, 2010. The entireties of the aforementioned applications are herein incorporated by reference.

FIELD

The present invention relates to the treatment of biomass to be used in the production of ethanol.

BACKGROUND

Ethanol can be produced from grain-based feedstocks (e.g., corn, sorghum/milo, barley, wheat, soybeans, etc.), from sugar (e.g., from sugar cane, sugar beets, etc.), and from biomass (e.g., from lignocellulosic feedstocks such as switchgrass, corn cobs and stover, wood or other plant material).

Biomass comprises plant matter that can be suitable for direct use as a fuel/energy source or as a feedstock for processing into another bioproduct (e.g., a biofuel such as cellulosic ethanol) produced at a biorefinery such as an ethanol plant. Biomass may comprise, for example, corn cobs and stover (e.g., stalks and leaves) made available during or after harvesting of the corn kernels, fiber from the corn kernel, switchgrass, farm or agricultural residue, wood chips or other wood waste, and other plant matter. In order to be used or processed, biomass will be harvested and collected from the field and transported to the location where it is to be used or processed.

In a conventional ethanol plant producing ethanol from corn, ethanol is produced from starch. Corn kernels are cleaned and milled to prepare starch-containing material for processing. Corn kernels may also be fractionated to separate the starch-containing material (e.g., endosperm) from other matter (e.g., fiber and germ). The starch-containing material is slurried with water and is liquefied to facilitate saccharification where the starch is converted into sugar (e.g., glucose) and fermentation where the sugar is converted by an ethanologen (e.g., yeast) into ethanol. The product of fermentation is beer, which comprises a liquid component containing ethanol, water, and soluble components, and a solids component containing unfermented particulate matter among other things. The fermentation product is sent to a distillation system where it is distilled and dehydrated to yield ethanol. The residual matter (e.g., whole stillage) comprises water, soluble components, oil and unfermented solids (i.e., the solids component of the beer with substantially all ethanol removed that can be dried into dried distillers grains (DDG) and sold as an animal feed product). Other co-products, for example syrup (and oil contained in the syrup), can also be recovered from the stillage. Water removed from the fermentation product in distillation can be treated for re-use at the plant.

In a biorefinery configured to produce ethanol from biomass, ethanol is produced from lignocellulosic material. Lignocellulosic biomass typically comprises cellulose, hemicellulose, and lignin. Cellulose (a type of glucan) is a polysaccharide comprising hexose (C6) sugar monomers such as glucose linked in linear chains. Hemicellulose is a branched chain polysaccharide that may comprise several different pentose (C5) sugar monomers (e.g., xylose and arabinose) and small amounts of hexose (C6) sugar monomers (e.g., mannose, galactose, rhamnose and glucose) in branched chains.

In a typical cellulosic process, the biomass is prepared so that sugars in the lignocellulosic material (e.g., glucose from the cellulose, and xylose from the hemicellulose) can be made accessible and fermented into a fermentation product containing ethanol. After fermentation, the fermentation product is distilled and dehydrated to yield ethanol.

In the preparation of the biomass for fermentation, the biomass is typically pretreated, for example, using an acid such as sulfuric acid. In order to achieve high ethanol concentration from the fermentation of acid-pretreated biomass (e.g., corn cobs), the C6 sugar-containing stream of the pretreated biomass is ideally fed into an enzyme hydrolysis reaction (i.e., a saccharification reaction) at a high solids loading. However, mixtures of acid-pretreated biomass (e.g., corn cobs) above about 10% solids are typically viscous and difficult to process in a traditional stirred tank reactor. As a result, it is typical for the enzymatic hydrolysis reaction to be carried out in either a fed batch mode or at a low solid loading. This lowers the efficiency of the process, however, and results in a lower concentration (i.e., a lower titer) of ethanol in the resulting fermentation product.

In view of the above, it would be advantageous to provide a system that provides one or more features to facilitate improvement in the efficiency and yield of ethanol from biomass.

SUMMARY

In one aspect, the invention relates to a biorefinery for producing a fermentation product from biomass comprising: (a) a system for preparing the biomass into prepared biomass; (b) a system for pre-treating the biomass into pre-treated biomass; (c) a separator for separating the pre-treated biomass into a first component comprising glucan and a second component comprising xylose; (d) a first treatment system for liquefying the first component by application of a first enzyme formulation into a liquefied first component; (e) a second treatment system for treating the liquefied first component into a treated first component by application of a second enzyme formulation so that glucose is made available; (f) a fermentation system configured to produce the fermentation product from the treated first component; wherein the fermentation product is produced by fermentation of glucose into ethanol; wherein the biomass comprises lignocellulosic material; wherein the lignocellulosic material comprises at least one of corn cobs, corn plant husks, corn plant leaves and corn plant stalks; and wherein the first enzyme formulation comprises a cellulase enzyme mixture.

In another aspect, the invention relates to a method for producing a fermentation product from biomass comprising: (a) preparing the biomass into prepared biomass; (b) pre-treating the biomass into pre-treated biomass; (c) separating the pre-treated biomass into a first component comprising glucan and a second component; (d) treating the first component by application of a first enzyme formulation into a liquefied first component; (e) treating the liquefied first component by application of a second enzyme formulation so that glucose is made available; (f) supplying an ethanologen to the treated first component so that the glucose can be converted to ethanol; wherein the first enzyme formulation comprises a cellulase enzyme mixture; wherein the biomass comprises lignocellulosic material; and wherein the lignocellulosic material comprises at least one of corn cobs, corn plant husks, corn plant leaves and corn plant stalks.

In an exemplary embodiment, the process features the use of a continuous stirred tank reactor (CSTR) to continuously liquefy the first component (i.e., the C6 stream comprising glucan) by enzymatic action. The liquefaction results in a reduction in viscosity of the C6 slurry thereby allowing it to be readily handled (e.g., pumped) at a higher solids loading in the downstream processes (e.g., enzyme hydrolysis and fermentation). The use of a higher solids loading enables the production of ethanol at a higher concentration from the process.

In a further aspect, the invention relates to a continuous process for making ethanol from biomass, the process comprising the steps of: (a) providing a continuous stirred tank reactor (CSTR) with an outlet stream that is in fluid communication with two or more batch reactors; (b) pre-treating the biomass into pre-treated biomass; (c) separating the pre-treated biomass into a C6 solid comprising glucan and a second component; (d) continuously feeding the C6 solid into the CSTR and treating the C6 solid with a first enzyme formulation in order to liquefy the C6 solid into a C6 slurry; (e) continuously feeding the C6 slurry from the CSTR into one or more of the batch reactors; wherein the C6 slurry is treated in the one or more batch reactors with a second enzyme formulation so that glucose is made available; and (f) fermenting the glucose to form a fermentation product comprising ethanol; wherein the biomass comprises lignocellulosic material selected from corn cobs, corn plant husks, corn plant leaves, corn plant stalks, and mixtures thereof; and wherein the first enzyme formulation comprises a cellulase enzyme mixture.

DESCRIPTION OF THE DRAWINGS

FIG. 8A and FIG. 8B list the composition of biomass comprising lignocellulosic plant material from the corn plant according to exemplary and representative embodiments.

FIG. 9A and FIG. 9B list the composition of the liquid component of pre-treated biomass according to exemplary and representative embodiments.

FIG. 10A and FIG. 10B list the composition of the solids component of pre-treated biomass according to exemplary and representative embodiments.

FIG. 11 shows exemplary operating conditions and data from the use of the system according to certain embodiments.

DETAILED DESCRIPTION

The embodiments as disclosed and described in the application (including the FIGURES and Examples) are intended to be illustrative and explanatory of the present inventions. Modifications and variations of the disclosed embodiments, for example, of the apparatus and processes employed (or to be employed) as well as of the compositions and treatments used (or to be used), are possible; all such modifications and variations are intended to be within the scope of the present inventions.

The word "exemplary" is used to mean serving as an example, instance, or illustration. Any embodiment or design described as "exemplary" is not necessarily to be construed as preferred or advantageous over other embodiments or designs, nor is it meant to preclude equivalent exemplary structures and techniques known to those of ordinary skill in the art. Rather, use of the word exemplary is intended to present concepts in a concrete fashion, and the disclosed subject matter is not limited by such examples.

The term "or" is intended to mean an inclusive "or" rather than an exclusive "or." To the extent that the terms "comprises," "has," "contains," and other similar words are used in either the detailed description or the claims, for the avoidance of doubt, such terms are intended to be inclusive in a manner similar to the term "comprising" as an open transition word without precluding any additional or other elements.

Figure 1A:
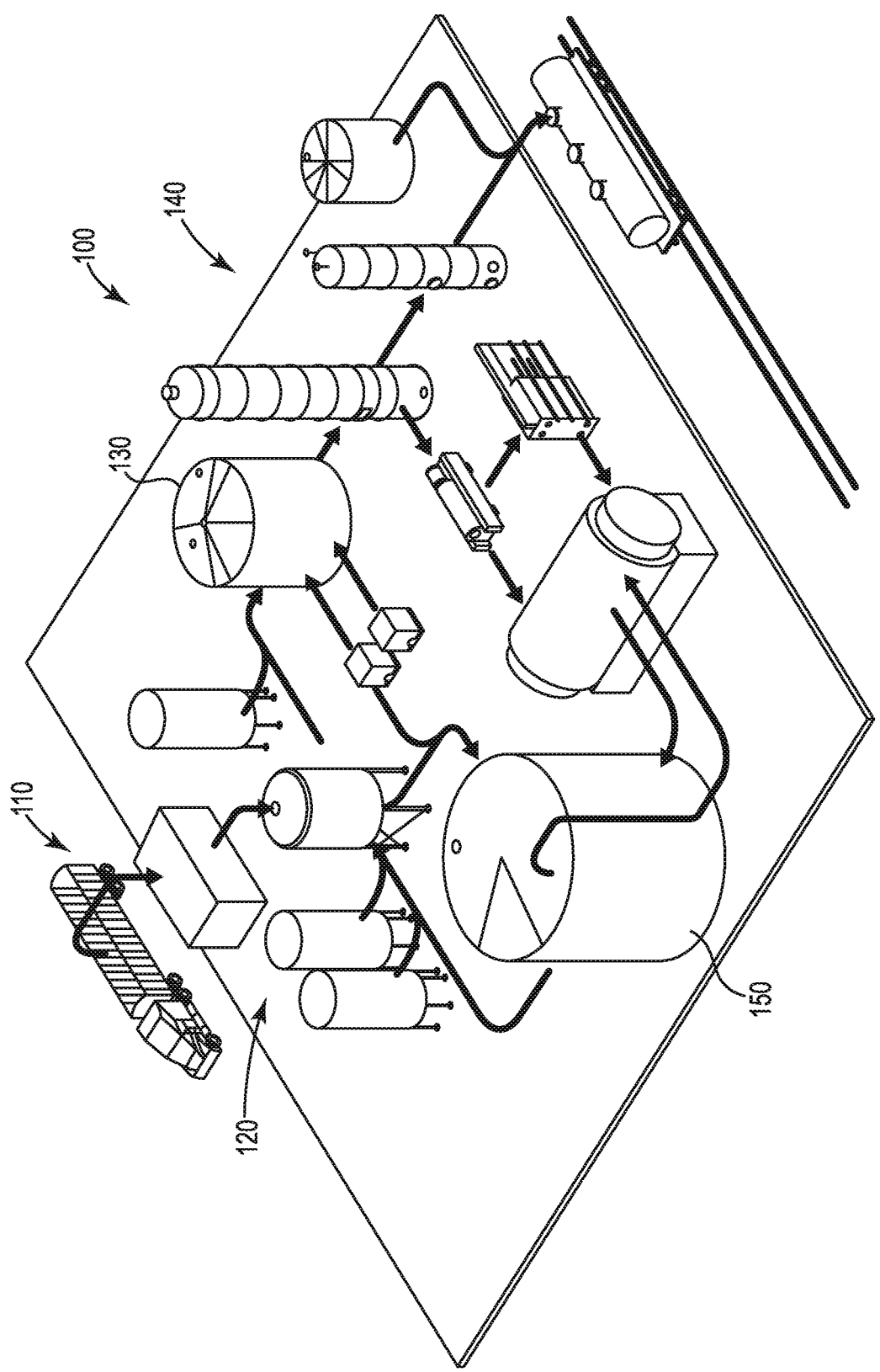
FIG. 1A is a perspective view of a biorefinery comprising a cellulosic ethanol production facility.

Referring to FIG. 1A, a biorefinery 100 configured to produce ethanol from biomass is shown. According to an exemplary embodiment, the biorefinery 100 is configured to produce ethanol from biomass in the form of a lignocellulosic feedstock such as plant material from the corn plant (e.g., corn cobs and corn stover). Lignocellulosic feedstock such as lignocellulosic material from the corn plant typically comprises cellulose (from which C6 sugars such as glucose can be made available) and/or hemicellulose (from which C5 sugars such as xylose and arabinose can be made available).

As shown in FIG. 1A, the biorefinery 100 comprises an area 110 where biomass is delivered and prepared to be supplied to the cellulosic ethanol production facility. The cellulosic ethanol production facility comprises apparatus 120 for preparation, pre-treatment, and treatment of the biomass into treated biomass suitable for fermentation into fermentation product in a fermentation system 130. The facility comprises a distillation system 140 in which the fermentation product is distilled and dehydrated into ethanol. As shown in FIG. 1A, the biorefinery may also comprise a waste treatment system 150 (shown as comprising an anaerobic digester and a generator). According to other alternative embodiments, the waste treatment system may comprise other equipment configured to treat, process, and recover components from the cellulosic ethanol production process, such as a solid/waste fuel boiler, anaerobic digester, aerobic digester, or other biochemical or chemical reactors.

Figure 1B:
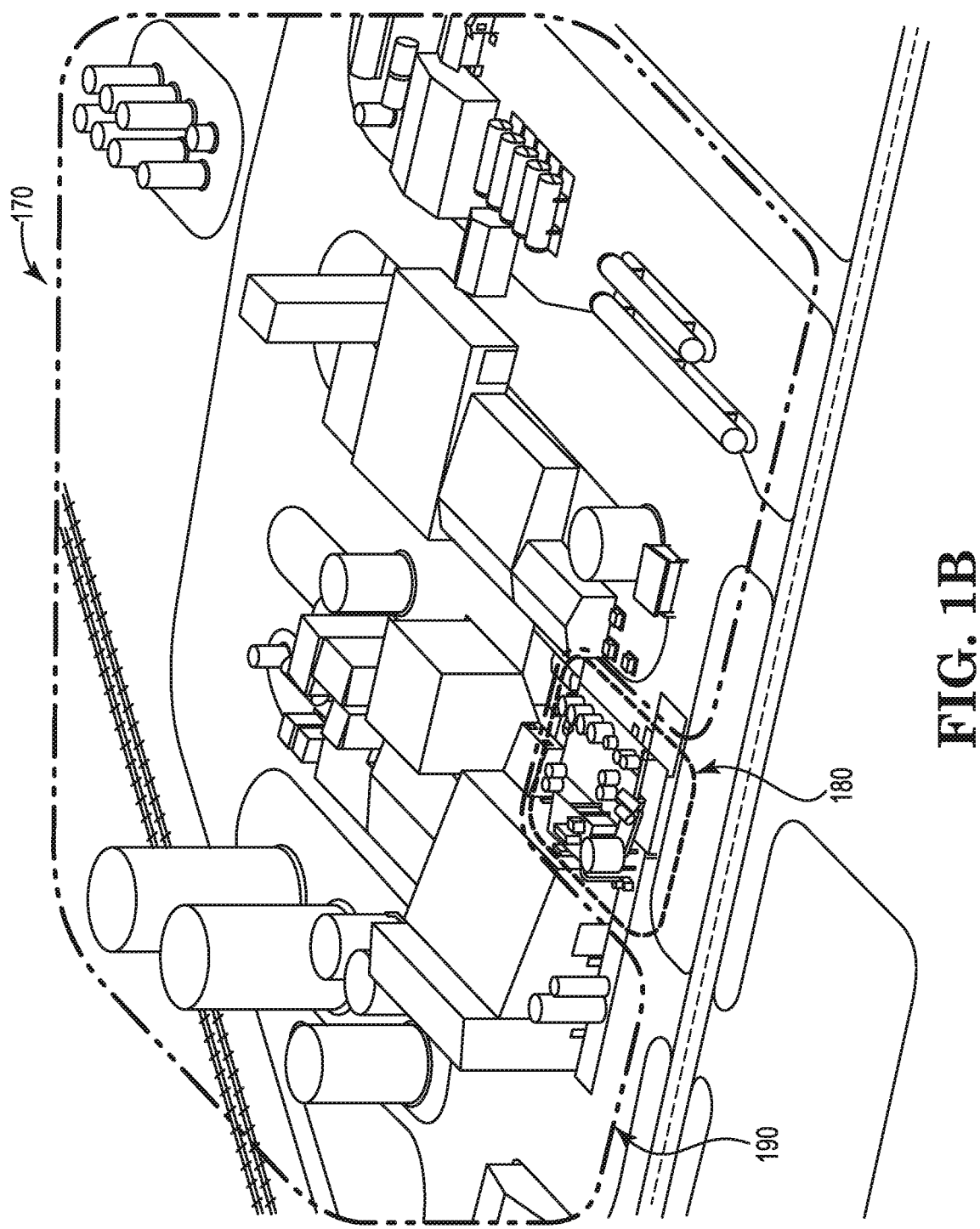
FIG. 1B is a perspective view of a biorefinery comprising a cellulosic ethanol production facility and a corn-based ethanol production facility.

As shown in FIG. 1B, according to an exemplary embodiment, a biorefinery 170 may comprise a cellulosic ethanol production facility 180 (which produces ethanol from lignocellulosic material and components of the corn plant) co-located with a corn-based ethanol production facility 190 (i.e., an ethanol plant that produces ethanol from starch contained in the endosperm component of the corn kernel).

As shown in FIG. 1B, by co-locating the two ethanol production facilities, certain plant systems may be shared, for example, systems for dehydration, storage, denaturing and transportation of ethanol, energy/fuel-to-energy generation systems, plant management and control systems, and other systems. Corn fiber (a component of the corn kernel), which can be made available when the corn kernel is prepared for milling (e.g., by fractionation) in the corn-based ethanol production facility, may be supplied to the cellulosic ethanol production facility as a feedstock. Fuel or energy sources such as methane or lignin from the cellulosic ethanol production facility may be used to supply power to either or both co-located facilities. According to other alternative embodiments, a biorefinery (e.g., a cellulosic ethanol production facility) may be co-located with other types of plants and facilities, for example an electric power plant, a waste treatment facility, a lumber mill, a paper plant, or a facility that processes agricultural products.

A biomass preparation system may comprise apparatus for receipt/unloading of the biomass, cleaning (i.e. removal of foreign matter), grinding (i.e. milling, reduction or densification), and transport and conveyance for processing at the plant. According to an exemplary embodiment, biomass in the form of corn cobs and stover may be delivered to the biorefinery and stored (e.g., in bales, piles or bins, etc.) and managed for use at the facility. According to an embodiment, the biomass may comprise at least about 20% to about 30% corn cobs (by weight) with corn stover and other matter. According to other exemplary embodiments, the preparation system of the biorefinery may be configured to prepare any of a wide variety of types of biomass (i.e. plant material) for treatment and processing into ethanol and other bioproducts at the plant.

In some embodiments, the biomass comprises plant material from the corn plant, such as corn cobs, husks and leaves and stalks (e.g., at least upper half or three-quarters portion of the stalk). In some embodiments, the composition of the plant material (i.e., cellulose, hemicellulose, and lignin) will be approximately as shown in TABLES 1A and 1B (i.e., after at least initial preparation of the biomass, including removal of any foreign matter). According to some embodiments, the plant material comprises corn cobs, husks/leaves and stalks; for example, the plant material may comprise up to 100% by weight cobs, up to 100% by weight husks/leaves, about 50% cobs and about 50% husks/leaves, about 30% cobs and about 50% husks/leaves and about 20% stalks. Any of a wide variety of other combinations of cobs, husks/leaves and stalks from the corn plant may also be useful. According to other embodiments, the lignocellulosic plant material may comprise fiber from the corn kernel (e.g., in some combination with other plant material). TABLE 1B provides ranges believed to be representative of the composition of biomass comprising lignocellulosic material from the corn plant. According to some embodiments, the lignocellulosic plant material of the biomass (from the corn plant) will comprise cellulose at about 30% to about 55% by weight, hemicellulose at about 20% to about 50% by weight, and lignin at about 10% to about 25% by weight. According to an exemplary embodiment, the lignocellulosic plant material of the biomass (i.e., cobs, husks/leaves and stalk portions from the corn plant) will comprise cellulose at about 35% to about 45% by weight, hemicellulose at about 24% to about 42% by weight, and lignin at about 12% to about 20% by weight.

Figure 2:
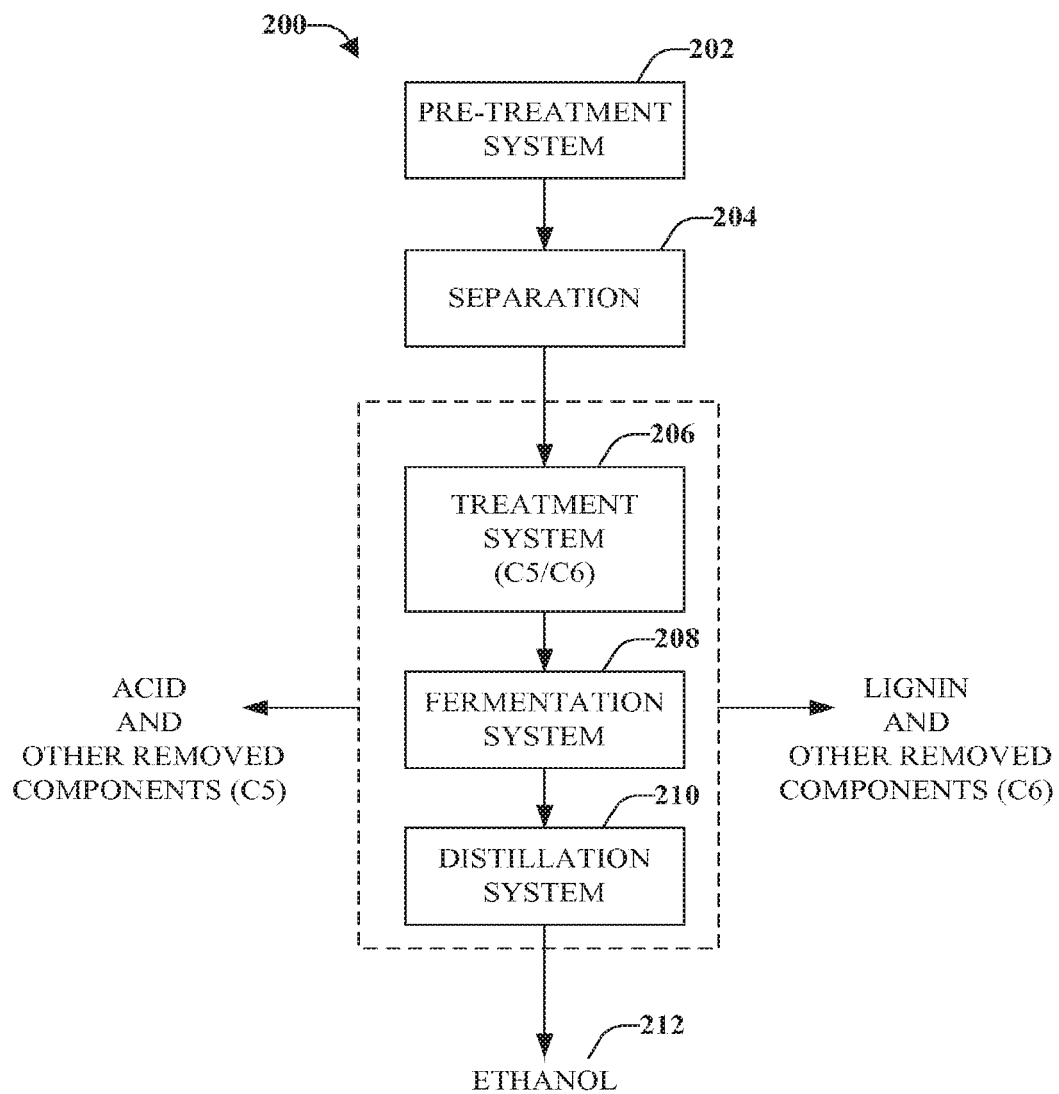
FIG. 2 is a schematic block diagram of a system for the production of ethanol from biomass.

Referring to FIG. 2, a schematic block diagram of a cellulosic ethanol production facility 200 is shown. According to an embodiment, biomass comprising plant material from the corn plant is prepared and cleaned at a preparation system. After preparation, the biomass is mixed with water to form a slurry, and is pre-treated at a pre-treatment system 202. In the pre-treatment system 202, the biomass is broken down (e.g., by hydrolysis) to facilitate separation 204 into a liquid stream (i.e., a stream comprising the C5 sugars) and a solids stream (i.e., a stream comprising cellulose from which the C6 sugars can be made available). The C5-sugar-containing liquid stream (C5 stream) and C6-sugar-containing solids stream (C6 stream) can be treated in a treatment system 206 (as may be suitable) and may be combined or may be retained as separate streams for fermentation in a fermentation system 208. Fermentation product from the fermentation system 208 is supplied to a distillation system 210 where ethanol 212 is recovered.

Figures 3A, 3B, 3C:
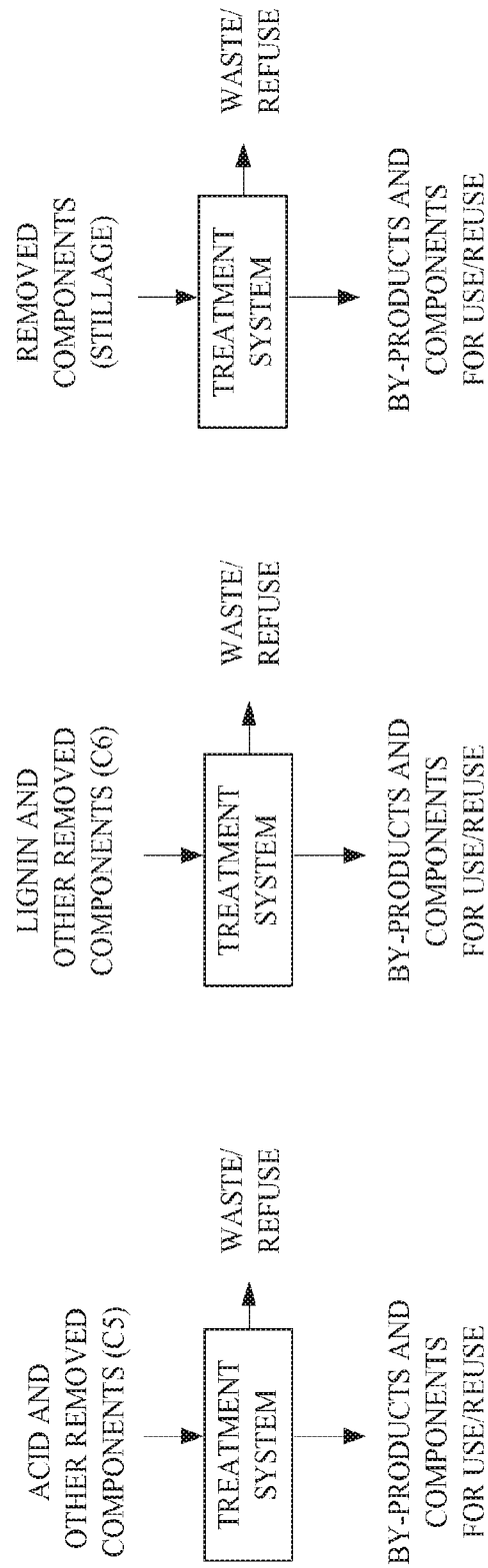
FIG. 3A, FIG. 3B and FIG. 3C are schematic block diagrams of systems for treatment and processing of components from the production of ethanol from biomass.

As shown in FIGS. 2 and 3A, removed components from treatment of the C5 stream can be treated or processed to recover by-products, such as organic acids and furfural. As shown in FIGS. 2 and 3B, removed components from treatment of the C6 stream, such as lignin or other components, can be treated or processed into bioproducts or into fuel (such as lignin for a solid fuel boiler or methane produced by treatment of residual/removed matter such as acids and lignin in an anaerobic digester). As shown in FIGS. 3A, 3B and 3C, components removed during treatment and production of ethanol from the biomass from either or both the C5 stream and the C6 stream (or at distillation) may be processed into bioproducts (e.g., by-products or co-products) or recovered for use or reuse. As shown in FIG. 3C, removed components from the distillation system (e.g., stillage or removed solids) or from the treatment of the fermentation product before distillation (e.g., removed solids and particulate matter, which may comprise residual lignin, etc.) can be treated or processed into bioproducts or fuel (e.g., methane produced in an anaerobic digester).

Figure 4A:
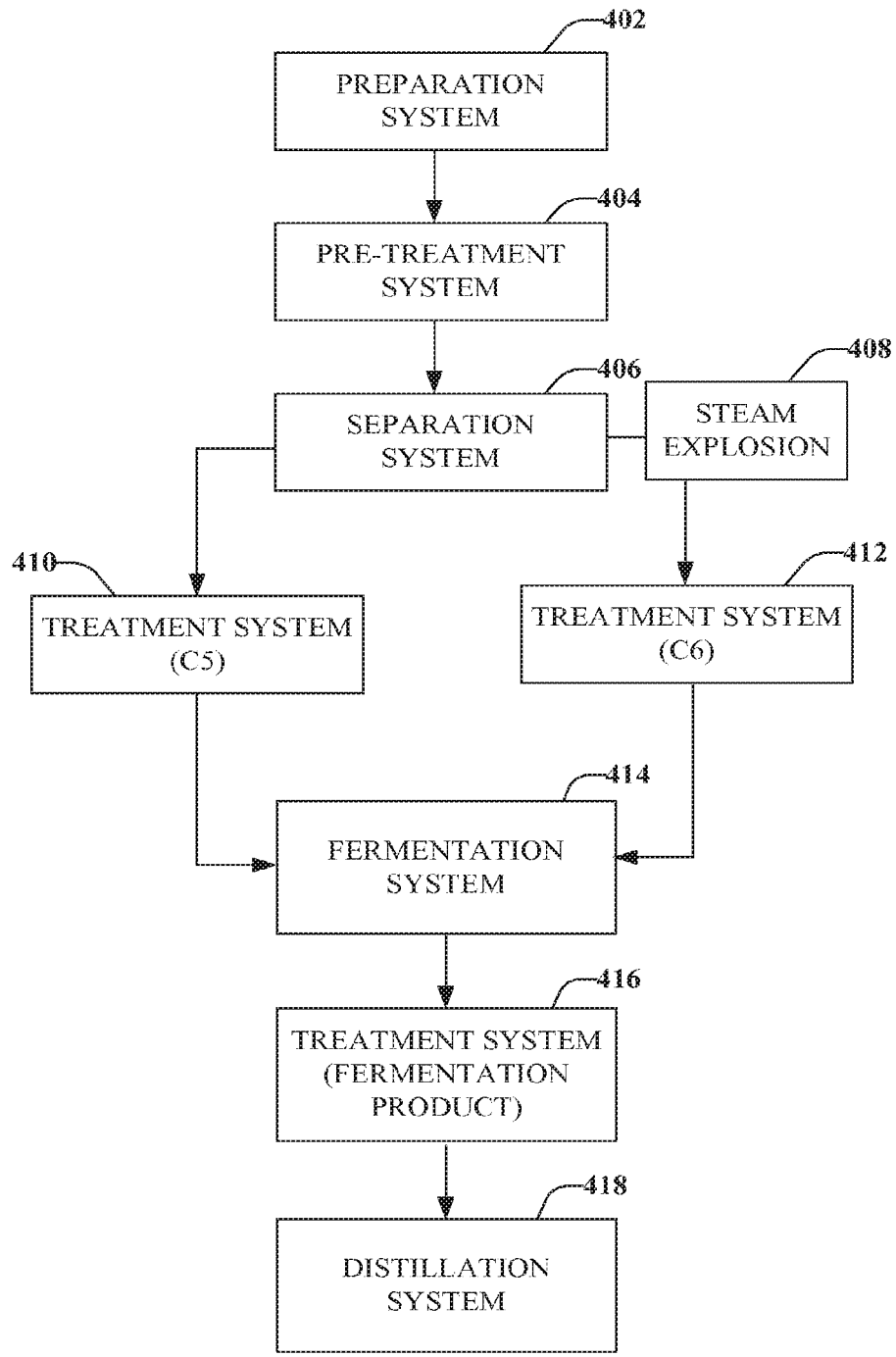
FIG. 4A and FIG. 4B are schematic block diagrams of systems for the production of ethanol from biomass.
Figure 4B:
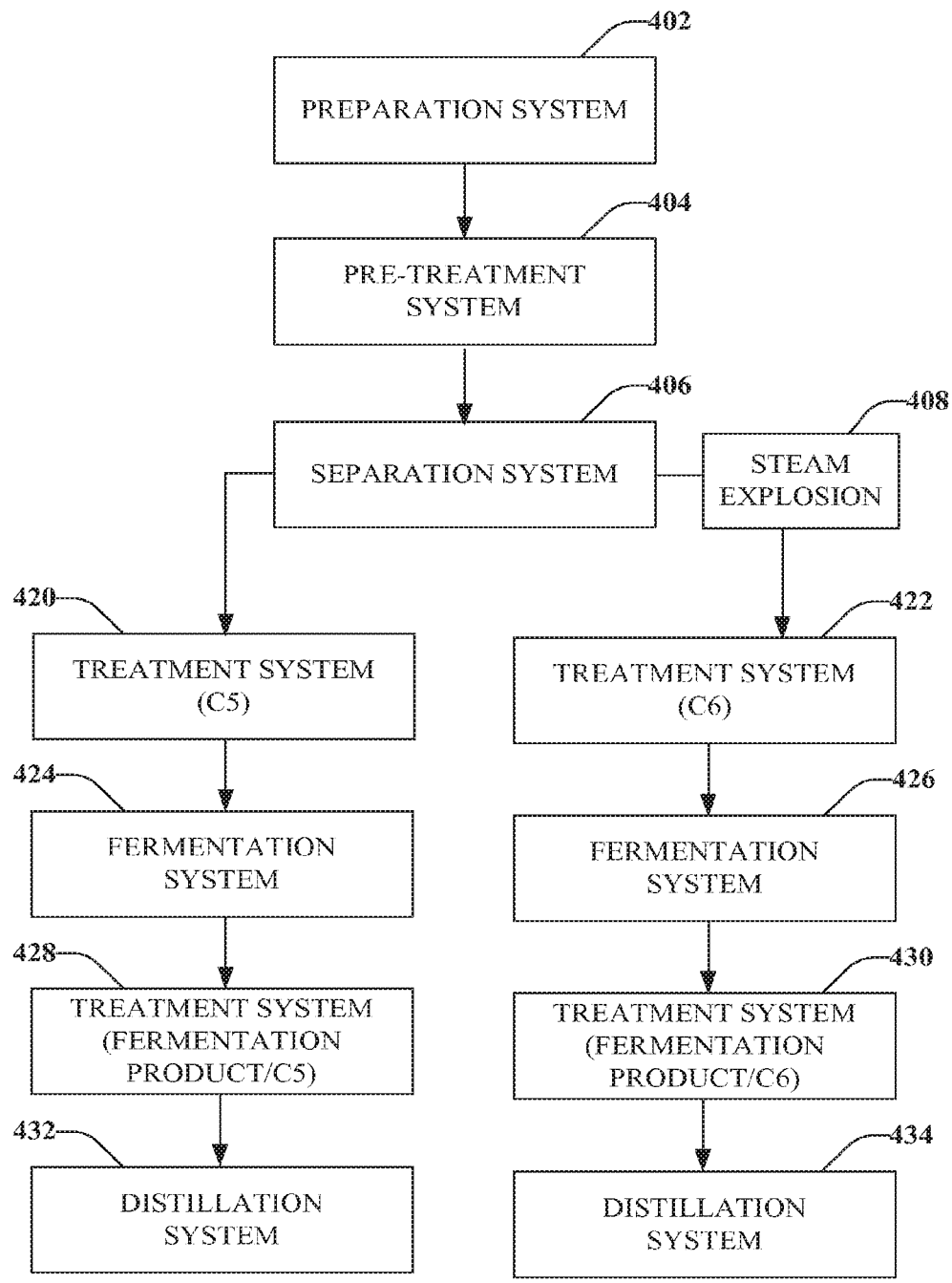

Referring now to FIGS. 4A and 4B, embodiments of systems for the production of ethanol from biomass are shown. As shown in FIGS. 4A and 4B, biomass is prepared in a preparation system 402, pre-treated in a pre-treatment system 404, and is then separated (in a separation system 406) into a liquid component (i.e., a C5 stream) and a solids component (i.e., a C6 stream) for further treatment and fermentation. The C5 and C6 stream may be combined for combined fermentation (see, FIG. 4A) or the C5 and C6 stream may be processed separately through fermentation (see, FIG. 4B).

According to an embodiment, in the pre-treatment system 404 an acid will be applied to the prepared biomass to facilitate the breakdown of the biomass for separation into the liquid component (i.e., the C5 stream from which fermentable C5 sugars can be recovered) and the solids component (i.e., the C6 stream from which fermentable C6 sugars can be accessed). According to an embodiment, the acid can be applied to the biomass in a reaction vessel under determined operating conditions (e.g., acid concentration, pH, temperature, time, pressure, solids loading, flow rate, supply of process water or steam, etc.), and the biomass can be agitated/mixed in the reaction vessel to facilitate the breakdown of the biomass. Useful acids include, for example, sulfuric acid, hydrochloric acid, nitric acid, phosphoric acid, acetic acid, and the like, or mixtures thereof. According to an exemplary embodiment, sulfuric acid is applied to the biomass in the pre-treatment system.

During pre-treatment, the severity of operating conditions (e.g., pH, temperature, and time) may cause formation of components that may be inhibitory to fermentation. For example, under some conditions, the dehydration of C5 sugars (e.g., xylose or arabinose) may cause the formation of furfural. Acetic acid may also be formed, for example, when acetate is released during the break down of hemicellulose in pre-treatment. Sulfuric acid, which may be added to prepared biomass to facilitate pre-treatment, may also be inhibitory to fermentation if not removed or neutralized. According to an exemplary embodiment, by adjusting pre-treatment conditions (e.g., pH, temperature, and time), the formation of inhibitors can be reduced or managed. According to some embodiments, components of the pre-treated biomass may be given further treatment to remove or reduce the level of inhibitors or other undesirable matter.

After pretreatment, the pre-treated biomass can then be separated into a liquid component (i.e., a C5 stream) and a solids component (i.e., a C6 stream) using a separation device such as a centrifuge (e.g., a decanter centrifuge, or basket centrifuge), screw press, or other type of solid-liquid separator.

After separation, the liquid component (i.e., the C5 stream) typically comprises water, dissolved sugars (e.g., xylose, arabinose, and glucose) for fermentation into ethanol, acids, and other soluble components recovered from the hemicellulose. TABLE 2B provides ranges believed to be representative of the composition of biomass comprising lignocellulosic material from the corn plant. According to some embodiments of the invention, the liquid component may comprise about 5% to about 7% solids by weight (i.e., suspended/residual solids such as partially-hydrolyzed hemicellulose, cellulose and lignin). According to other embodiments, the liquid component may comprise about 2% to about 4% xylose by weight. According to yet other embodiments, the liquid component may comprise no less than about 1% to about 2% xylose by weight. TABLES 2A and 2B list the composition of the liquid component of pre-treated biomass (prepared from the biomass as indicated in TABLES 1A and 1B). According to an exemplary embodiment, pre-treatment of the biomass will yield a liquid component that comprises xylose at no less than about 1.0% by weight and a solids component that comprises cellulose (from which glucose can be made available) at no less than about 45% by weight.

After separation, the solids component (i.e., the C6 stream) typically comprises water, acids, and solids (e.g., cellulose which is a source of glucose), and lignin. TABLE 3B provides ranges believed to be representative of the composition of biomass comprising lignocellulosic material from the corn plant. According to some embodiments of the invention, the solids component may comprise about 10% to about 40% solids by weight after separation. According to other embodiments of the invention, the solids component will comprise about 20% to about 30% solids by weight. According to yet other embodiments, the solids in the solids component comprise no less than about 30% by weight cellulose, and the solids component may further comprise other dissolved sugars such as glucose and xylose. TABLES 3A and 3B list the composition of the solids component of pre-treated biomass prepared from the biomass as indicated in TABLES 1A and 1B.

Figure 5:
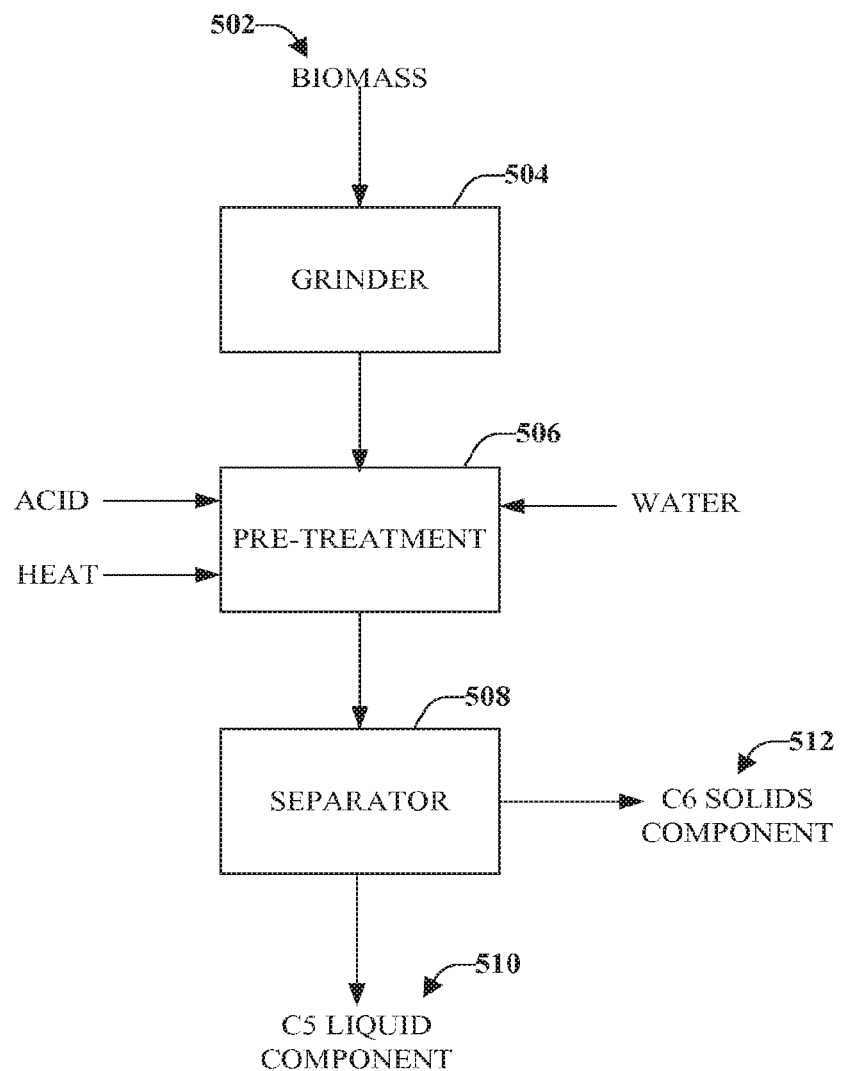
FIG. 5 is a schematic block diagram of a system for the preparation, pre-treatment, and separation of biomass.

Referring now to FIG. 5, an exemplary apparatus for preparation, pre-treatment and separation of lignocellulosic biomass according to embodiments of the invention. As shown, biomass 502 is prepared in a grinder 504 or other suitable apparatus or mill pre-treatment 506 of the prepared biomass is performed in a reaction vessel (or set of reaction vessels) supplied with prepared biomass and acid/water in a predetermined concentration (or pH) and other operating conditions. The pre-treated biomass is then separated 508 (e.g., using a centrifuge or screw press) into a liquid component 510 (i.e., a C5 stream comprising primarily liquids with some solids) and a solids component 512 (i.e., a C6 stream comprising liquids and solids (e.g., lignin and cellulose)).

Referring now to FIGS. 4A and 4B, after separation, the C6 stream may be steam exploded 408 (i.e., exposed to high temperature/pressure steam followed by explosive discharge to a lower pressure) in order to reduce its particle size and render it more accessible to enzymatic treatment. Typical conditions for steam explosion include steam treatment at about 170° C. to about 190° C. for about 2 to about 8 minutes, followed by rapid depressurization.

According to an embodiment as shown in FIG. 4A, after pre-treatment and separation, the C5 stream and the C6 stream can be treated separately 410, 412 and subsequently combined (e.g., as a slurry) for co-fermentation in the fermentation system 414 to produce a C5/C6 fermentation product from the available sugars (e.g., xylose and glucose). The C5/C6 fermentation product can (after treatment 416, if any) be supplied to the distillation system 418 for recovery of the ethanol (e.g., through distillation and dehydration). According to another embodiment, as shown in FIG. 4B, the C5 stream and the C6 stream can each be separately processed through treatment 420, 422, fermentation 424, 426, treatment 428, 430 (if any), and distillation 432, 434 to produce ethanol.

In some embodiments, the C5 stream (liquid component) is treated to remove components that are inhibitory to efficient fermentation (e.g., furfural, HMF, sulfuric acid and acetic acid) and to remove residual lignin or other matter that may not be fermentable. The C5 sugars in the C5 stream may also be concentrated to improve the efficiency of fermentation (e.g., to improve the titer of ethanol for distillation).

Treatment of the C6 stream (solids component) of the biomass may be performed to make the C6 sugars available for fermentation. As discussed further herein, the C6 stream may also be treated in order to liquefy (i.e., reduce the viscosity) of the C6 stream so that it can be more readily handled (e.g., pumped) in the downstream process. The C6 stream may also be treated by enzyme hydrolysis to access the C6 sugars in the cellulose. Treatment may also be performed in an effort to remove lignin and other non-fermentable components in the C6 stream or to remove components such as residual acid or acids that may be inhibitory to efficient fermentation.

In the fermentation system, a suitable fermenting organism (i.e., an ethanologen) is typically used. The selection of an ethanologen may be based on various considerations including, for example, the predominant types of sugars present in the slurry. Dehydration and/or denaturing of the ethanol produced from the C5 stream and the C6 stream may be performed either separately or in combination.

Figure 6A:
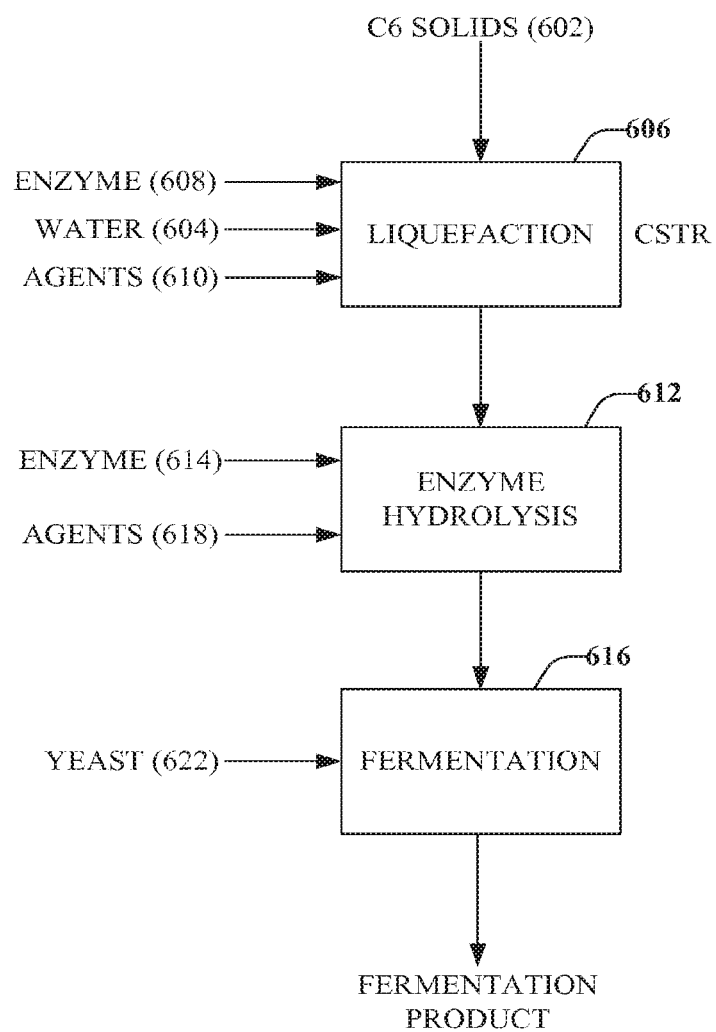
FIG. 6A and FIG. 6B are schematic block diagrams of a treatment system for treating a C6 solids component.
Figure 6B:
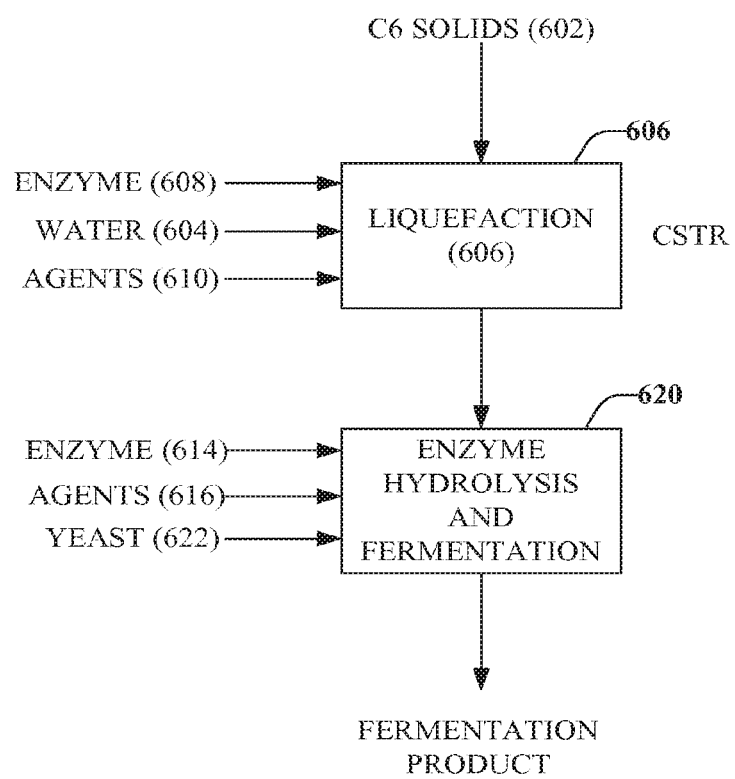

Referring now to FIG. 4B, according to an exemplary embodiment, the biorefinery may comprise a treatment system and fermentation system for the C6 stream (solids component) that is separate from the treatment system and fermentation system for the C6 stream. As shown in FIGS. 6A and 6B, the C6 stream (solids component 602) can be mixed with water 604 to form a slurry and supplied to a tank (e.g., a vessel with agitation, such as a continuously stirred tank reactor (CSTR)) for liquefaction 606 to facilitate partial break down of cellulose and to reduce the viscosity of the slurry. According to an exemplary embodiment, an enzyme formulation (e.g., comprising a cellulase enzyme mixture 608) is supplied to the C6 stream in the vessel to facilitate liquefaction by enzyme action of the polymeric cellulose (e.g., polymeric glucan) into partially hydrolyzed cellulose (e.g., oligomeric glucan) and monomeric sugars (e.g., monomeric glucose). The amount or loading (dose) of enzyme formulation may be varied as an operating condition. Agents 610 (e.g., potassium hydroxide or ammonia for pH adjustment) may also be supplied to the slurry. The treated (i.e., liquefied) slurry comprises at least partially hydrolyzed cellulose (glucan) and glucose. According to an exemplary embodiment, the enzyme formulation comprises a cellulase enzyme mixture available under the trade name Cellic CTEC2 from Novozymes North America, Inc. (Franklinton, N.C.).

As shown in FIGS. 6A and 6B, the liquefied slurry is then sent to a vessel for enzyme hydrolysis 612 (i.e., saccharification). In the vessel, the liquefied C6 stream is treated by adding an enzyme formulation 614 to facilitate enzyme hydrolysis (i.e., the saccharification). In enzyme hydrolysis 612, the enzyme acts on the polymeric cellulose (e.g., polymeric glucan) and partially hydrolyzed cellulose (e.g., oligomeric glucan) to form a hydrolysate comprising glucose that is available for fermentation 616. The amount or loading (dose) of the enzyme formulation may be varied as an operating condition. Agents 618 (e.g., potassium hydroxide or ammonia for pH adjustment) may also be supplied to the slurry. According to an exemplary embodiment, the enzyme formulation will comprise a cellulase enzyme mixture available under the trade name Cellic CTEC2 from Novozymes North America, Inc. (Franklinton, N.C.).

In some embodiments, as shown in FIG. 6A, the enzyme hydrolysis 612 and fermentation 616 are conducted in separate vessels. Alternatively, as shown in FIG. 6B, the treated (i.e., liquefied) C6 stream may undergo enzymatic hydrolysis and fermentation simultaneously in a vessel 620 that contains both an enzyme formulation 614 and an ethanologen (i.e., yeast 622) under suitable operating conditions. In this simultaneous process, glucan and partially hydrolyzed glucan are converted by enzyme hydrolysis (i.e., saccharification) into glucose, and the glucose is available for conversion into ethanol by the ethanologen (e.g., yeast) that is present in the vessel.

Figure 7:
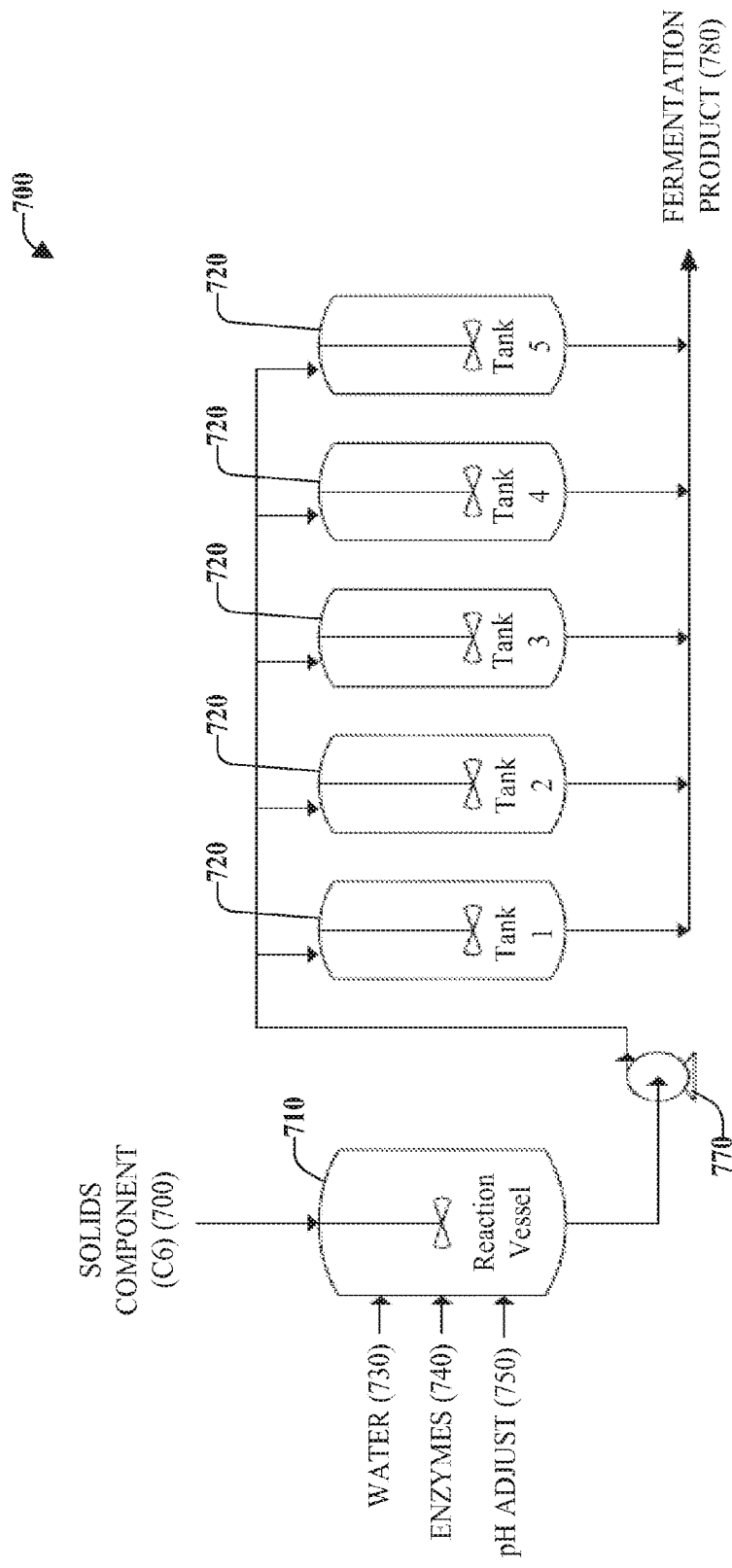
FIG. 7 is a process diagram of a liquefaction process according to an exemplary embodiment.

Referring now to FIG. 7, an exemplary apparatus 700 for treatment of a C6 slurry (e.g., liquefied C6 solid) is shown. As shown in FIG. 7, the C6 solids component 700 of the pre-treated biomass is fed as a slurry into a continuous stirred tank reactor (CSTR) 710. The CSTR 710 is in fluid communication with 2 or more (e.g., 5 are shown in FIG. 7) batch reactors 720. The CSTR 710 includes feed inlets for continuously supplying C6 solids 700, water 730, enzyme 740, and pH adjustment 750 to the CSTR 710. The CSTR 710 includes a mixer 760, and is equipped with temperature control. The C6 slurry of the solids component typically comprises solids, water, and residual acid from the pre-treatment system. According to an exemplary embodiment where the biomass comprises corn cobs and stover and has been pre-treated with sulfuric acid and separated into a liquid component and solids component, the C6 slurry of the solids component will comprise about 10% to about 30% solids with the remainder as liquid. The C6 slurry typically comprises cellulose (glucan) and lignin (as well as xylan, among other things) in the solids as well as dissolved sugars (e.g., xylose and glucose) in the liquid/water portion of the slurry. The pH of the slurry can be increased to a suitable level for enzymatic liquefaction, for example, by the addition of a base such as potassium hydroxide or ammonium hydroxide. Liquefaction of the C6 slurry is conducted under specified operating conditions (e.g., time, temperature, enzyme loading, pH, etc.) in the CSTR in order to partially break down the cellulose (glucan). The liquefaction (first enzyme) can comprise endoglucanase activity. The partial breakdown of the cellulose (glucan) results in liquefaction and a reduction in the viscosity of the C6 slurry. Enzymatic liquefaction allows a slurry that has a high solids loading (e.g., greater than about 10% solids dry weight) to be readily pumped into downstream batch reactors 720 where enzyme hydrolysis (i.e., saccharification) and, optionally, fermentation are conducted. The hydrolysis (second enzyme) can comprise a mixture containing cellobiohydrolase and beta-glucosidase activities. Specifically, once enzymatically liquefied, the C6 slurry can be pumped by pump 770 into one or more of the batch reactors 720 for enzyme hydrolysis and optionally fermentation. Upon completion of enzyme hydrolysis and fermentation the resulting fermentation product 780 can be treated and distilled to provide ethanol. The continuous enzymatic liquefaction allows a high solids loading to be processed through fermentation in order to provide a higher ethanol titer in the fermented product.

Typically, the continuous enzyme liquefaction process is conducted at a solids loading ranging from about 10% to about 30% solids dry weight; more typically ranging from about 10% to about 25% solids dry weight; and most typically about 13% to about 17% solids dry weight.

With respect to enzyme loading (e.g., using Cellic CTEC2 enzyme), a typical range is about 2 to about 20 mg of enzyme protein per gram of glucan, more typically ranging from about 3 to about 9 mg of enzyme protein per gram of glucan, and most typically ranging from about 4 to about 6 mg of enzyme protein per gram of glucan.

With respect to pH, continuous enzymatic liquefaction is typically conducted at an acidic pH. A typical pH range is from about 4.0 to about 6.0, more typically from about 4.5 to about 6.0, and most typically about 5.0 to about 6.0.

Continuous enzymatic liquefaction is typically conducted at a temperature ranging from about 30° C. to about 60° C., more typically ranging from about 45° C. to about 55° C., and most typically ranging from about 49° C. to about 51° C.

The residence time for continuous enzyme liquefaction in the CSTR typically ranges from about 1 hour to about 30 hours, more typically ranging from about 4 hours to about 16 hours, and most typically ranging from about 8 to about 12 hours.

The invention will now be further described with reference to the following non-limiting examples.

Examples

A sample of solids component (C6 stream) was prepared as a slurry comprising a solids loading of about 15% with about 57% glucan (by dry weight of the solids). The sample was treated in a continuously stirred tank reactor (CSTR) under operating conditions as indicated in TABLE 4. The pH of the sample was adjusted to about pH 5.7. An enzyme formulation was added to the sample at a concentration of about 6 mg of enzyme protein per gram of glucan. (The enzyme formulation comprised a cellulase enzyme available under the trade name Celtic CTEC2 from Novozymes North America.) Treatment of the sample by liquefaction through the application of the enzyme formulation was performed at a temperature of about 50° C. with a retention time of about 10 hours. The sample/slurry after liquefaction (i.e. liquefied solids component) was supplied to the fermentation system for combined enzyme hydrolysis/fermentation into ethanol. It was observed that the viscosity of the sample (slurry)

could be reduced by treatment (liquefaction) as to facilitate effective operation at a solids loading of about 15%. It was also observed that treatment and fermentation of samples could be performed continuously for a period of about 35 days at a solids loading of about 15%. It was further observed that liquefaction increased the glucose concentration into the solids component from about 1% to about 2%.

What is claimed is:

1. A method for producing a fermentation product from biomass comprising:
    (a) preparing the biomass into prepared biomass;
    (b) pre-treating the biomass into pre-treated biomass comprising polymeric glucan;
    (c) continuously supplying the pretreated biomass to a liquefaction stirred reactor;
    (d) continuously treating the pretreated biomass by application of a first enzyme formulation to at least partially hydrolyze at least a portion of the polymeric glucan into oligomeric glucan and glucose and form a liquefied component, wherein the liquefaction stirred reactor is in parallel fluid communication with two or more batch saccharification stirred reactors of a batch saccharification system so that the liquefaction stirred reactor can operate in a continuous manner, wherein the first enzyme formulation comprises a cellulase enzyme mixture, and wherein the first enzyme formulation comprises endoglucanase activity, wherein a viscosity of the pretreated biomass is reduced during the continuously treating the pretreated biomass by application of the first enzyme formulation, wherein the continuously treating the pretreated biomass by application of the first enzyme formulation is performed at a solids loading from 10% to 30% solids dry weight, and wherein a retention time of the pretreated biomass in the continuously treating the pretreated biomass by application of the first enzyme formulation is from 1 hour to 30 hours;
    (e) continuously supplying liquefied component to the batch saccharification system to supply liquefied component to each of the two or more batch saccharification reactors, wherein a portion of the liquefied component is supplied to a first of the two or more batch saccharification stirred reactors;
    (f) treating the portion of the liquefied component by application of a second enzyme formulation to hydrolyze polymeric glucan and oligomeric glucan to form a saccharified component so that glucose is made available, wherein treating occurs in the first batch saccharification stirred reactor according to a batch process, wherein the second enzyme formulation comprises a cellulase enzyme mixture, and wherein the second enzyme formulation comprises cellobiohydrolase activity and betaglucosidase activity;
    (g) supplying the saccharified component to a fermentation reactor;
    (h) supplying an ethanologen to the saccharified component so that the glucose can be converted to ethanol; and
    (i) supplying an additional portion of the liquefied component to a second of the two or more batch saccharification stirred reactors,
    wherein the biomass comprises lignocellulosic material; and
    wherein the lignocellulosic material comprises at least one of corn cobs, corn plant husks, corn plant leaves and corn plant stalks.

2. The method of claim 1, wherein the first enzyme formulation is supplied at a concentration of about 1 to 20 mg of enzyme protein per gram of glucan during the step of treating the pretreated biomass into the liquefied component.

3. The method of claim 2, comprising the step of maintaining a pH of the pretreated biomass in a range of pH 4 to 6 during the step of treating the pretreated biomass into the liquefied component.

4. The method of claim 3, comprising the step of maintaining a temperature of the pretreated biomass in a range of about 30° C. to about 60° C. during the step of treating the pretreated biomass into the liquefied component.

5. The method of claim 4, wherein the pre-treating the biomass comprises utilizing an acid pre-treatment system.

6. The method of claim 5, wherein the pretreated biomass comprises a solids component of the lignocellulosic material.

7. The method of claim 6, wherein the pretreated biomass comprises lignin.

8. The method of claim 7, wherein the pretreated biomass comprises solids in a range of about 13% to about 17% by weight during the step of treating the pretreated biomass into the liquefied component.

9. The method of claim 1, wherein the polymeric glucan comprises cellulose and the first enzyme formulation is capable of liquefying polymeric glucan.

10. The method of claim 1, wherein the lignocellulosic material consists essentially of corn cobs, corn plant husks, corn plant leaves and corn stalks.

11. A method for producing a fermentation product from biomass comprising:
    continuously supplying a lignocellulosic biomass and a cellulase enzyme to a liquefaction system, wherein the lignocellulosic biomass comprises cellulose, wherein the cellulase comprises endoglucanase activity, and wherein the liquefaction system is in parallel fluid communication with two or more batch saccharification stirred reactors of a batch saccharification system so that the liquefaction system can operate in a continuous manner;
    continuously enzymatically hydrolyzing the cellulose to at least partially hydrolyze at least a portion of the cellulose into oligomeric glucan and glucose and form a liquefied component, wherein a viscosity of the lignocellulosic biomass is reduced during the continuously enzymatically hydrolyzing the cellulose to form the liquefied component, wherein the continuously enzymatically hydrolyzing the cellulose to form the liquefied component is performed at a solids loading from 10% to 30% solids dry weight, and wherein a retention time of the lignocellulosic biomass in the continuously enzymatically hydrolyzing the cellulose to form the liquefied component is from 1 hour to 30 hours;
    continuously supplying the liquefied component to the batch saccharification system to supply liquefied component to each of the two or more batch saccharification reactors, wherein a portion of the liquefied component is supplied to a first of the two or more batch saccharification stirred reactors;
    enzymatically hydrolyzing the portion of the liquefied component to hydrolyze cellulose and oligomeric glucan in the portion of the liquefied component to form a first saccharified component comprising glucose, wherein enzymatically hydrolyzing the portion of the liquefied component occurs in the first batch saccharification stirred reactor according to a batch process;

supplying an ethanologen and the first saccharified component to a fermentation reactor so that the glucose can be converted to ethanol;

supplying an additional portion of the liquefied component to a second of the two or more batch saccharification stirred reactors;

enzymatically hydrolyzing the additional portion of the liquefied component to hydrolyze cellulose and oligomeric glucan in the additional portion of the liquefied component to form a second saccharified component comprising glucose, wherein enzymatically hydrolyzing the additional portion of the liquefied component occurs in the second batch saccharification stirred reactor according to a batch process.

12. The method of claim 11, wherein enzymatically hydrolyzing the portion of the liquefied component comprises applying a second enzyme formulation to hydrolyze cellulose and oligomeric glucan in the portion of the liquefied component, wherein the second enzyme formulation comprises cellobiohydrolase activity and betaglucosidase activity.

* * * * *

UNITED STATES PATENT AND TRADEMARK OFFICE
CERTIFICATE OF CORRECTION

PATENT NO. : 10,533,203 B2
APPLICATION NO. : 13/638238
DATED : January 14, 2020
INVENTOR(S) : David Charles Carlson Page 1 of 1

It is certified that error appears in the above-identified patent and that said Letters Patent is hereby corrected as shown below:

In the Specification

Column 5
Line 39 "TABLES 1A and 1B" should be -- FIGS. 8A and 8B --
Line 51 "TABLE 1B" should be -- FIG. 8B --

Column 7
Line 24 "TABLE 2B" should be -- FIG. 9B --
Lines 34-35 "TABLES 2A and 2B" should be -- FIGS. 9A and 9B --
Line 37 "TABLES 1A and 1B)" should be -- FIGS. 8A and 8B) --
Lines 45-46 "TABLE 3B" should be -- FIG. 10B --
Lines 56-57 "TABLES 3A and 3B" should be -- FIGS. 10A and 10B --
Line 59 "TABLES 1A and 1B" should be -- FIGS. 8A and 8B --

Column 10
Line 55 "TABLE 4" should be -- FIG. 11 --

Signed and Sealed this
Twenty-fifth Day of August, 2020

Andrei Iancu
*Director of the United States Patent and Trademark Office*